United States Patent
Gabizon et al.

(10) Patent No.: US 9,937,261 B2
(45) Date of Patent: Apr. 10, 2018

(54) COMBINATION THERAPY COMPRISING A LIPOSOMAL PRODRUG OF MITOMYCIN C AND RADIOTHERAPY

(71) Applicants: LIPOMEDIX PHARMACEUTICALS LTD., Jerusalem (IL); THE UNIVERSITY OF NORTH CAROLINA AT CHAPEL HILL, Chapel Hill, NC (US)

(72) Inventors: Alberto Gabizon, Jerusalem (IL); Patricia Ohana, Jerusalem (IL); Andrew Wang, Chapel Hill, NC (US)

(73) Assignees: Lipomedix Pharmaceuticals Ltd., Jerusalem (IL); The University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 15/317,842

(22) PCT Filed: Jun. 9, 2015

(86) PCT No.: PCT/US2015/034897
§ 371 (c)(1),
(2) Date: Dec. 9, 2016

(87) PCT Pub. No.: WO2015/191576
PCT Pub. Date: Dec. 17, 2015

(65) Prior Publication Data
US 2017/0119895 A1 May 4, 2017

Related U.S. Application Data

(60) Provisional application No. 62/120,637, filed on Feb. 25, 2015, provisional application No. 62/009,767, filed on Jun. 9, 2014.

(51) Int. Cl.
*A61K 9/127* (2006.01)
*A61K 47/48* (2006.01)
*A61K 31/407* (2006.01)

(52) U.S. Cl.
CPC ........ *A61K 47/48046* (2013.01); *A61K 9/127* (2013.01); *A61K 31/407* (2013.01)

(58) Field of Classification Search
CPC ..................................................... A61K 9/127
See application file for complete search history.

(56) References Cited

U.S. PATENT DOCUMENTS 6,365,179 B1 * 4/2002 Zalipsky .............. A61K 9/0019
                                                     205/254
6,787,132 B1    9/2004 Gabizon et al.
(Continued)

FOREIGN PATENT DOCUMENTS

WO    WO 2015/191563 A1    12/2015
WO    WO 2016/191876 A1    12/2015

OTHER PUBLICATIONS

Chen et al., "No survival benefit from postoperative adjuvant chemotherapy after D2 radical resection for the patients with stage II gastric cancer", Am. J. Clin. Oncol., vol. 34, No. 3, pp. 309-313 (2011).

(Continued)

*Primary Examiner* — Benjamin Packard
(74) *Attorney, Agent, or Firm* — McDermott Will & Emery LLP

(57) ABSTRACT

A method of treating neoplasia in a subject in need of treatment is provided by administering to the subject an amount of a prodrug of mitomycin C that yields a therapeutically effective amount of mitomycin C, in combination with radiation therapy. In one embodiment, the prodrug of mitomycin C is a liposomal-prodrug of mitomycin C.

(Continued)

Together, the prodrug of mitomycin C and radiation therapy provide a synergistic antineoplastic effect.

20 Claims, 7 Drawing Sheets

(56) References Cited

U.S. PATENT DOCUMENTS

| | | | |
|---|---|---|---|
| 6,984,396 B2 | 1/2006 | Zalipsky et al. | |
| 7,303,760 B2 | 12/2007 | Zalipsky et al. | |
| 2004/0013660 A1 | 1/2004 | Bissery | |
| 2004/0161455 A1* | 8/2004 | Zalipsky | A61K 31/407 424/450 |
| 2009/0131367 A1* | 5/2009 | Gore | A61K 31/435 514/64 |
| 2017/0119895 A1 | 5/2017 | Gabizon et al. | |

OTHER PUBLICATIONS

Cheung et al., "In vivo efficacy and toxicity of intratumorally delivered mitomycin C and its combination with doxorubicin using microsphere formulations", Anti-Cancer Drugs, vol. 16, No. 4, pp. 423-433 (2005).

Cheung et al., "In vitro toxicity to breast cancer cells of microsphere-delivered mitomycin C and its combination with doxorubicin", Eur. J. Pharm. Biopharm., vol. 62, No. 3, pp. 321-331 (2006).

Gabizon et al., "Reduced Toxicity and Superior Therapeutic Activity of aMitomycin CLipid-Based Prodrug Incorporated in Pegylated Liposomes", Clinical Cancer Research, vol. 12, No. 6, pp. 1913-1920 (2006).

Galanis et al., "Phase I-II trial of ONYX-015 in combination with MAP chemotherapy in patients with advanced sarcomas", Gene Ther., vol. 12, No. 5, pp. 437-445 (2005).

Ghanaati et al., "Efficacy of transarterial chemoembolization on lesion reduction in colorectal liver metastases", Acta. Med. Iran., vol. 50, No. 8, pp. 535-540 (2012).

Gibson et al., "Phase II study of 5-fluorouracil, doxorubicin, and mitomycin C for metastatic small bowel adenocarcinoma", Oncologist, vol. 10, No. 2, pp. 132-137 (2005).

Gnad-Vogt et al., "Pegylated liposomal doxorubicin and mitomycin C in combination with infusional 5-fluorouracil and sodium folinic acid in the treatment of advanced gastric cancer: results of a phase II trial", Anticancer Drugs, vol. 16, No. 4, pp. 435-440 (2005).

Hofheinz et al., "Treatment of a patient with advanced esophageal cancer with a combination of mitomycin C and capecitabine: activation of the thymidine phosphorylase as active principle?", Onkologie, vol. 26, No. 2, pp. 161-164 (2003).

International Search Report from PCT Patent Application No. PCT/US2015/034670 dated Aug. 24, 2015, application now published as International Publication No. WO2015/191563 dated Dec. 17, 2015.

International Search Report from PCT Patent Application No. PCT/US2015/034897 dated Aug. 24, 2015, application now published as International Publication No. WO2015/191576 dated Dec. 17, 2015.

Kawano et al., "Synergistic antitumor activity of interleukin-2, mitomycin C and 5-fluorouracil against colon cancer", Proc. Am. Assoc. Cancer Res., vol. 35, No. 0, p. 323, Abst. 1920 (1994).

Kornek et al., "Combined radiochemotheray of locally advanced unresectable pancreatic adenocarcinoma with mitomycin C plus 24-hour continuous infusional gemcitabine", Int. J. Radiat. Oncol. Biol. Phys., vol. 49, No. 3, pp. 657-671 (2001).

Kostkova et al., "HPMA copolymer conjugates of DOX and mitomycin C for combination therapy: physicochemical characterization, cytotoxic effects, combination index analysis, and antitumor efficacy", Macromol. Biosci., vol. 13, No, 2, pp. 1648-1660 (2013).

Lee et al., "Second-line treatment with a combination of continuous 5-fluorouracil, doxorubicin, and mitomycin-C (conti-FAM) in gemcitabine-pretreated pancreatic and biliary tract cancer", Am. J. Olin. Oncol., vol. 32, No. 4, pp. 348-352 (2009).

Lewis et al, "Mitomycin C (MMC) combined with paclitaxel (PCTX)—A clinical and pharmacokinetic study", Clinical Pharmacology and Therapeutics, vol. 65, No. 2, p. 198, Abst. PIII-89 (1999).

Ludgate et al., "Synchronous 5-fluorouracil, Mitomycin-C and radiation therapy in the treatment of locally advanced carcinoma of the cervix", Int. J. Rad. Oncol. Biol. Phys., vol. 15, No. 4, pp. 893-899 (1988).

Misra et al., "Intrahepatic arterial infusion with combination of Mitomycin C (MMC) and 5-Flurouracil (5-FU) for treatment of Primary and Metastatic Carcinoma of Liver", Reg. Cancer Treat, vol. 1-2, pp. 12-16 (1992).

Opyrchal et al., "Phase I clinical trial of locoregional administration of the oncolytic adenovirus ONYX-015 in combination with mitomycin-C, doxotubicin, and cisplatin chemotherapy in patients with advanced sarcomas", Methods Mol. Biol., vol. 542, p. 705-717 (2009).

Patterson et al., "Prodrugs in genetic chemoradiotherapy", Curr. Pharm. Des., vol. 9, No. 26, pp. 2131-2154 (2003).

Peters et al., "Synergism of gemcitabine (GEM) with etoposide (VP), mitomycine C (MMC) and LY231514 (LY)", Proc. Amer. Cancer Res., vol. 38, No. 0, p. 319, Abst. 2136 (1997).

Prasad et al., "Doxorubicin and mitomycin C co-loaded polymer-lipid hybrid nanoparticles inhibit growth of sensitive and multidrug resistant human mammary tumor xenografts", Cancer Letters, vol. 334, No. 2, pp. 263-273 (2013).

Rockwell, "Combination therapy with radiation, mitomycin C, and 5-fluorouracil in EMT6 tumors", Int. J. Radiation Oncology Biol. Phys., vol. 28, No, 1, pp. 127-133 (1994).

Saif et al., "S-1: a promising new oral fluoropyrimidine derivative", Expert Opin. Investig. Drugs, vol. 18, No. 3, pp. 335-348 (2009).

Shuhendler et al., "On the synergistic effect of doxorubicin and mitomycin C against breast cancer cells", Drug Metabol. Drug Interact., vol. 22, No. 4, pp. 201-233 (2007).

Shuhendler et al., "A novel doxorubicin-mitomycin C co-encapsulated nanoparticie formulation exhibits anti-cancer synergy in multidrug resistant human breast cancer cells", Breast Cacner Res. Treat, vol. 119, No. 2, pp. 255-269 (2009).

Toyama et al., "A case of postoperative liver metastasis from pancreatic carcinoma treated with percutaneous isolated hepatic perfusion(PIHP)", Gan To Kagaku Ryoho, vol. 39, No. 12, pp. 1886-1888 (2012) English Abstract.

Yonemoto et al., "A multi-center retrospective analysis of survival benefits of chemotherapy for unresectable biliary tract cancer", Jpn. J. Clin. Oncol., vol. 37, No. 11, pp. 843-851 (2007).

* cited by examiner

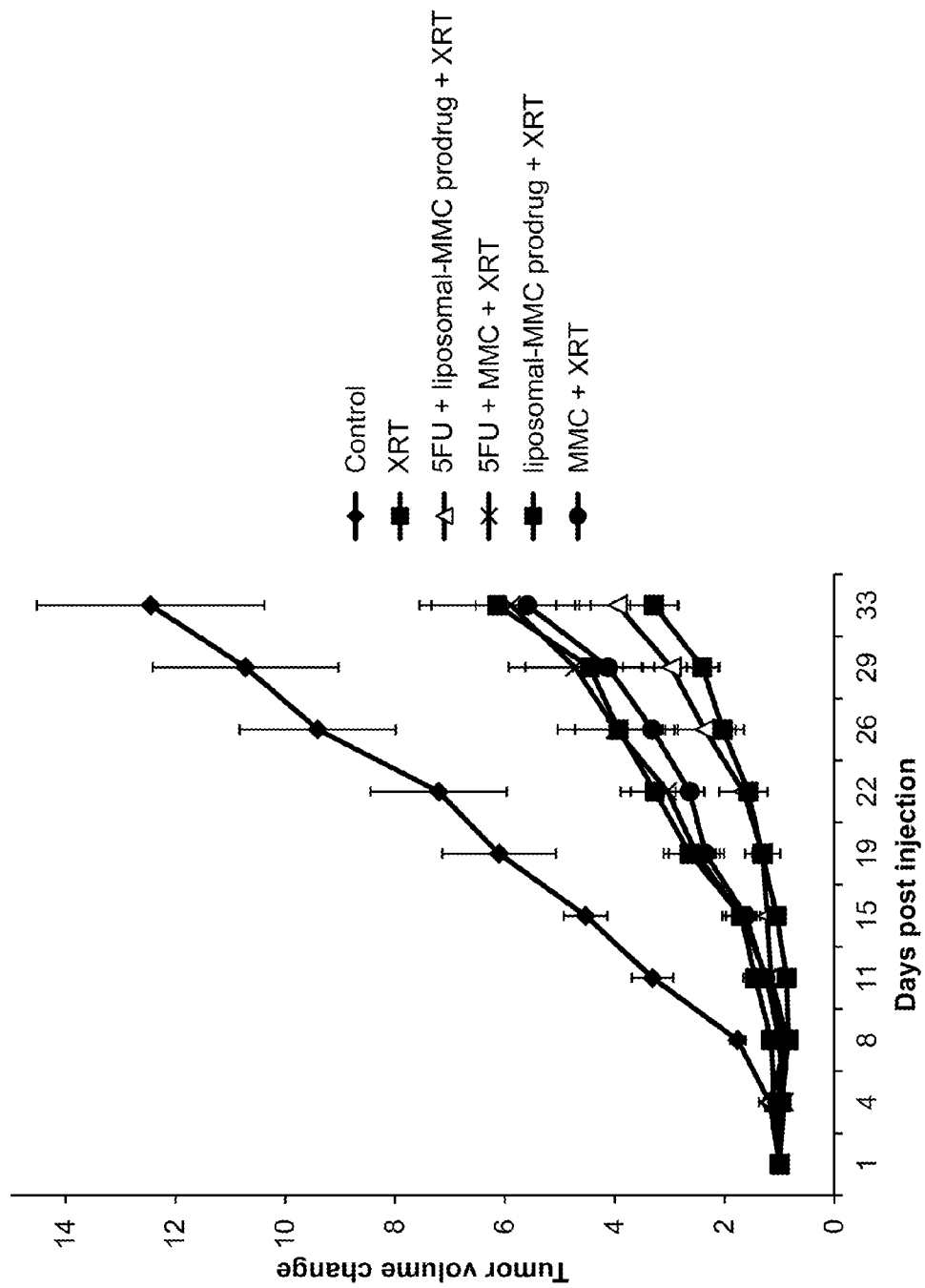

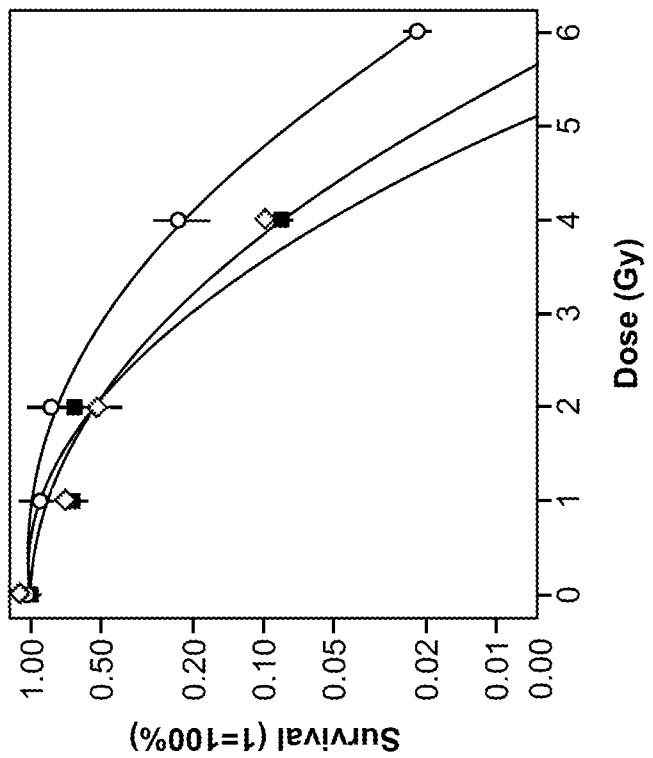
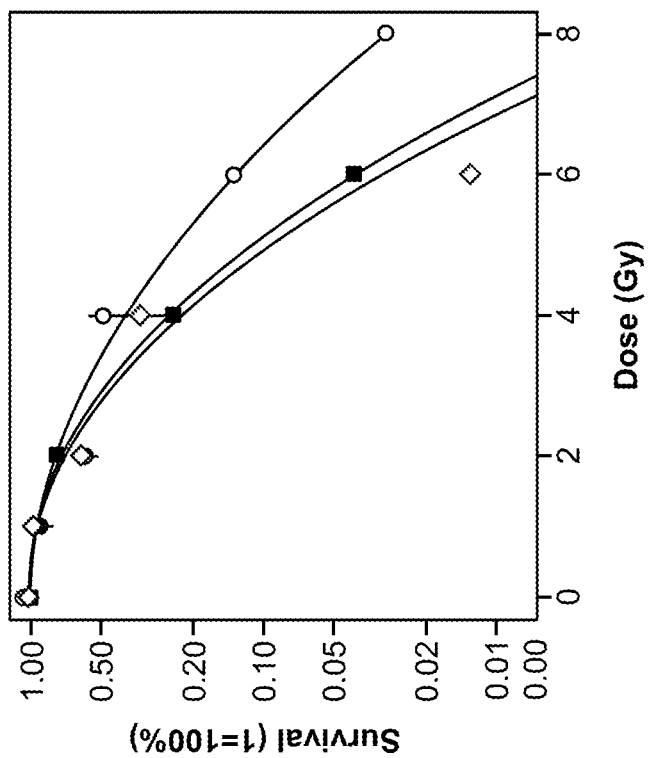
FIG. 4D
FIG. 4C

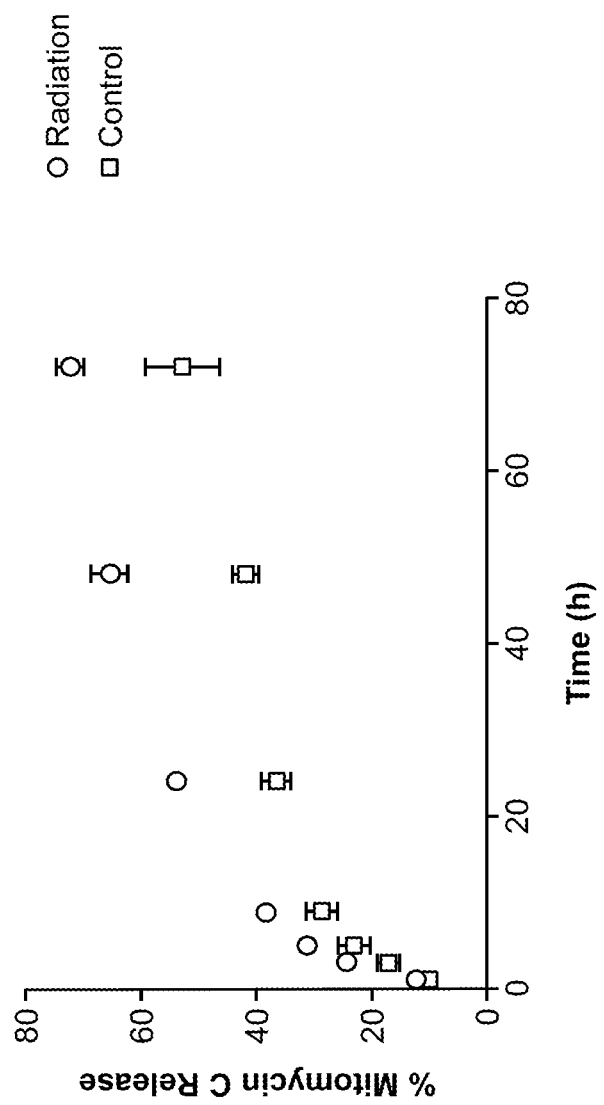

… (US 9,937,261 B2)

COMBINATION THERAPY COMPRISING A LIPOSOMAL PRODRUG OF MITOMYCIN C AND RADIOTHERAPY

CROSS-REFERENCE TO RELATED APPLICATIONS

This application is a U.S. National Stage of International Patent Application No. PCT/US2015/034897, filed Jun. 9, 2015, which claims the benefit of U.S. Provisional Application No. 62/009,767, filed Jun. 9, 2014, and of U.S. Provisional Application No. 62/120,637, filed Feb. 25, 2015, each of which is incorporated by reference herein in its entirety.

TECHNICAL FIELD

The subject matter described herein relates to methods for treating patients in need of treatment for a neoplastic condition by a combination of a liposomal prodrug of mitomycin C and radiotherapy.

BACKGROUND

Cancer is a leading cause of death in the United States and affects people worldwide. Surgery, radiation therapy and chemotherapy are the most widely used therapeutic modalities. Development of new treatment regimens for cancer therapy that provide synergistic effects and minimal toxicity to the subject being treated would be advantageous.

BRIEF SUMMARY

The following aspects and embodiments thereof described and illustrated below are meant to be exemplary and illustrative, not limiting in scope.

In one aspect, a method of treatment is provided. The method comprises providing to a subject in need a prodrug of mitomycin C in an amount that yields a therapeutically-effective amount of mitomycin C; and instructing to administer, or administering, in combination with the prodrug a radiotherapy treatment.

In one embodiment, the prodrug is a conjugate of mitomycin C releasably attached to a lipophilic moiety. In one embodiment, the lipophilic moiety is incorporated into a liposome, and in another embodiment, the lipophilic moiety is incorporated into a bilayer of a liposome.

In another embodiment, providing a prodrug of mitomycin C comprises providing via injection a prodrug of mitomycin C. In another embodiment, providing a prodrug of mitomycin C comprises providing via injection a liposome containing a prodrug of mitomycin C. In yet another embodiment, providing a prodrug of mitomycin C comprises providing a composition comprising a liposomal formulation, where the prodrug of mitomycin C is incorporated into liposomes in the liposomal formulation.

In yet another embodiment, providing via injection comprises intravenous, intraarterial, intraperitoneal, intrapleural, intrathecal, intravesical or intratumoral injection.

In another aspect, a method of treatment is provided. The method comprises providing to a subject in need a prodrug of mitomycin C in an amount that yields a therapeutically-effective amount of mitomycin C; and instructing to administer, or administering, in combination with the prodrug, radiation therapy and/or a second chemotherapeutic agent that is not the prodrug or free mitomycin C.

In one embodiment, instructing comprises instructing to administer the radiotherapy treatment prior to, concurrently or sequentially with the prodrug.

In another aspect, a treatment regimen for a subject with a neoplasm (e.g., cancer) comprises administering a prodrug of mitomycin C in an amount that yields a therapeutically-effective amount of mitomycin C; and administering a type of radiotherapy, where the combined therapy provides a reduction in tumor volume or a prolongation in survival of the subject, when compared to that achieved by administering the prodrug and/or free mitomycin C and/or the radiotherapy alone.

In one embodiment, the treatment regimen comprises administering a second chemotherapeutic agent that is not the prodrug or mitomycin C as a free agent. The radiation therapy combined with the prodrug of mitomycin C, alone or in combination with a second chemotherapeutic agent, provides a reduction in tumor volume or a prolongation in survival of the subject, when compared to that achieved by administering the prodrug alone and/or the second chemotherapeutic agent alone and/or radiotherapy treatment alone.

In one embodiment, the neoplasm in the patient is a cancer brain cancer, head and neck cancer, lung cancer, breast cancer, esophageal cancer, stomach cancer, pancreatic cancer, colorectal cancer, or bladder cancer.

In yet another aspect, a method for treating a solid tumor is provided. The method comprises providing a prodrug of mitomycin C in an amount that yields a therapeutically-effective amount of mitomycin C; and providing instructions to administer in combination with radiation therapy.

In on embodiment, instructions are provided to administer the radiation therapy prior to, concurrently or sequentially with administering the prodrug.

In yet another aspect, a product comprised of a vial containing a prodrug of mitomycin C in an amount that yields a therapeutically-effective amount of mitomycin C and instructions to administer the contents within the vial in combination with radiation therapy is provided.

Additional embodiments of the present methods will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIG. 3B shows the change in tumor volume (ratio of tumor volume at indicated day post chemotherapeutic agent injection to tumor volume at day of injection (day 1)) as a function of days post injection of chemotherapeutic agent in mice bearing a human colon cancer tumor (SW480), where mice were left untreated (control, solid diamonds), treated with radiotherapy (irradiation) (solid squares), treated with radiotherapy (irradiation) and liposomal-mitomycin C prodrug (* symbols), treated with irradiation and free mitomycin C (closed circles), treated with radiotherapy (irradiation) and a combination therapy of liposomal-mitomycin C prodrug and 5-fluorouracin (open triangles), or treated with radiotherapy (irradiation) and a combination therapy of free mitomycin C and 5-fluorouracil (x symbols);

FIGS. 4C-4D are graphs showing the percent survival (1=100%) of HT29 cells (FIG. 4C) and SW480 cells (FIG. 4D) as a function of radiation dose, in Gy, where the cells were treated with free mitomycin C (squares) or with liposomal-mitomycin C prodrug (open diamonds) at equivalent doses and exposed to radiotherapy at various doses; and FIG. 5 is a graph of percent of mitomycin C released after cleavage of prodrug from the liposomal formulation as a function of time, in hours, when cells are incubated in the presence of liposomal-mitomycin C prodrug and irradiated with 20 Gy x-ray therapy (circles), or when cells are incubated in the presence of liposomal-mitomycin C prodrug but not treated with x-ray irradiation (control; squares).

DETAILED DESCRIPTION

Definitions

Figure 1:
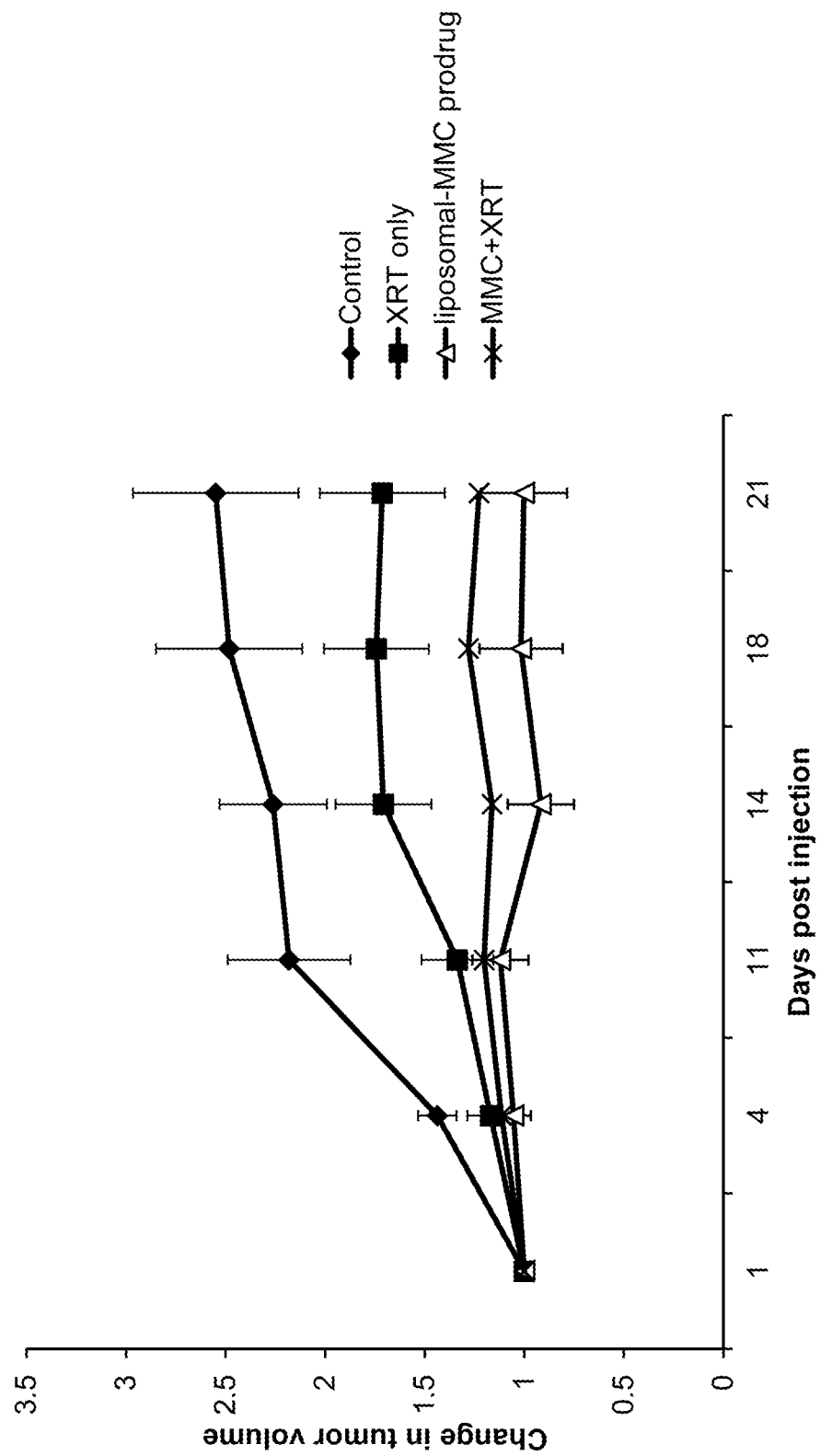
FIG. 1 shows the change in tumor volume (ratio of tumor volume at day zero to tumor volume at indicated day post injection) as a function of days post injection of the chemotherapeutic agent in mice bearing a squamous cell carcinoma tumor (CaSki) and left untreated (control, solid diamonds), treated with radiotherapy (irradiation, solid squares), treated with radiotherapy (irradiation) and liposomal-mitomycin C prodrug (open triangles) or treated with radiotherapy (irradiation) and free mitomycin C (x symbols)

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

"Administering" or "administration" as used herein means the introduction of a foreign molecule into a cell or host. The term is intended to be synonymous with the term "delivery" or "delivering". Suitable routes of administration, without limitation, are intravenous, intra-arterial, intramuscular, subcutaneous, intraperitoneal, intrapleural, intrathecal, intravesical or intratumoral, intrasynovial, infusion, sublingual, transdermal, oral, or topical.

As used herein, the phrase "chemotherapeutic agent" is synonymous with and "antineoplastic agent" or "antiproliferative agent" and refers to compounds that prevent cancer, or hyperproliferative cells, from multiplying. Generally, antineoplastic agents may prevent cancer cells from multiplying by: (1) interfering with the cell's ability to replicate DNA and (2) inducing cell death and/or apoptosis in the cancer cells.

An amount of liposomal-mitomycin C prodrug that yields a therapeutically-effective amount of mitomycin C after administration is an amount of mitomycin C that is effective to ameliorate or minimize the clinical impairment or symptoms of the neoplasia, in either a single or multiple doses.

As used herein, a "neoplasm" or "neoplasia" means a proliferative disease characterized by the abnormal proliferation of cells. Typically, neoplasia is associated with cancer and tumor formation. As used herein a "solid tumor" is one that occurs in an organ, such as the breast or the colon.

The term "patient" refers to an individual afflicted with a disease characterized by neoplasia. In particular, a patient (i.e., a host) is an animal (i.e., mammal) or human.

As used herein, "pharmaceutical formulations" include formulations for human and veterinary use with no significant adverse effect. "Pharmaceutically acceptable carrier" as used herein refers to a composition or formulation that allows for the effective distribution of the agents of the instant invention in the physical location most suitable for their desired activity and "pharmaceutically acceptable carrier" refers to a buffer, stabilizer or other material well known to those skilled in the art. Such materials should be non-toxic and should not interfere with the efficacy of the active ingredient. The precise nature of the carrier or other material may depend on the route of administration.

As used herein, "prodrug" means a compound that is a drug precursor which, following administration to a subject, releases the drug in vivo via some chemical or physiological process such that the prodrug is converted into a product that is toxic to cells of a neoplasm.

As used herein "synergistic effect" or "therapeutic synergy" refers to a clinical observation wherein a combination of liposomal-mitomycin C prodrug and radiotherapy provides more than additive effect of the liposomal-mitomycin C prodrug alone and the radiotherapy alone.

"Radiotherapy" intends a treatment using x-rays (irradiation) or a radioactive substance; it is also referred to herein as "radiation therapy" or "radiation treatment."

Reference to a "therapeutically effective amount," intends an amount of a compound sufficient to show benefit to the individual. This amount prevents, alleviates, abates, or otherwise reduces the severity of a symptom associated with neoplasia in a patient, such as a reduction in tumor mass or volume or a slowing of tumor growth rate.

The terms "treat," "treatment" and "therapeutic effect" as used herein refer to reducing or stopping a cell proliferation rate (e.g., slowing or halting tumor growth) or reducing the number of proliferating cancer cells.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "liposome" includes a single liposome as well as two or more of the same or different liposomes, reference to an "excipient" includes a single excipient as well as two or more of the same or different excipients, and the like.

Methods of Treatment

In one aspect, a method for treating a subject comprises providing a prodrug of mitomycin C in an amount that yields a therapeutically-effective amount of mitomycin C, and administering, or instructing to administer, in conjunction with administration of the prodrug, radiotherapy. As will be illustrated below, the prodrug of mitomycin C and the radiotherapy provide a synergistic effect.

Liposomal Mitomycin C Prodrug

The liposomal prodrug conjugate of mitomycin C provided for use in the methods described herein is, in one embodiment, comprised of mitomycin C releasably attached to a lipophilic or hydrophobic moiety, and generally is of the form:

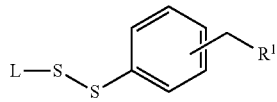

wherein L is a hydrophobic moiety, $R^1$ represents a mitomycin C residue covalently attached to the dithiobenzyl moiety. Orientation of the $CH_2R^1$ group is selected from the ortho position and the para position. Synthesis of the conjugate is described in U.S. Pat. Nos. 6,365,179; 6,984,396; and 7,303,760, each of which is incorporated by reference herein.

The hydrophobic moiety, L, is typically a lipid such as a diacylglycerol, a sterol, a phospholipid, derivatives of these lipids, other naturally-occurring lipids and their synthetic analogs. The hydrophobic moiety is suitable for incorporation into a liposomal bilayer, to anchor the mitomycin C conjugate to a liposomal delivery vehicle.

The liposomal-mitomycin C prodrug conjugate upon exposure to reducing conditions, i.e., a reducing agent such as cysteine or glutathione, decomposes to yield mitomycin C. That is, thiolytic cleavage of the conjugate yields mitomycin C and non-toxic by products of the hydrophobic moiety and the dithiobenzyl moiety. As can be appreciated, the prodrug conjugate can be readily incorporated into liposomes for administration in vivo to a subject. The prodrug conjugate is not toxic, and after administration and upon exposure to endogenous reducing agents or exposure to an exogenous reducing agent, the conjugate decomposes to yield mitomycin C in its native state and with biological activity.

Studies conducted in support of the methods described herein used the prodrug conjugate para-diacyldiglyceroldithiobenzyl-mitomycin C. The prodrug conjugate ortho-diacyldiglyceroldithiobenzyl-mitomycin C can also be utilized.

The conjugate was synthesized as set forth in Example 1 and was incorporated into a liposomal delivery vehicle, also as described in Example 1.

Radiotherapy

Radiation therapy uses high-energy radiation to damage and/or kill cancer cells and to shrink tumors. The high-energy radiation may involve x-rays, gamma rays or charged particles. The radiation therapy may be delivered by a machine positioned outside the body (external-beam radiation therapy), or it may come from radioactive material placed in the body near cancer cells (internal radiation therapy, also called brachytherapy). Systemic radiation therapy uses radioactive substances, such as radioactive iodine, that travel in the blood to kill cancer cells.

Accordingly, in one embodiment, radiotherapy intends external radiotherapy where the radiation comes from an instrument outside the body. External radiotherapy is usually given as a course of several treatments over days or weeks and during a treatment a machine directs the high-energy radiation, usually X-rays, at the cancer site and a small area of normal tissue surrounding it.

In another embodiment, radiotherapy intends internal radiotherapy where the radiation comes from an implant or a material (liquid, solid, semi-solid or other substance) placed inside the body. In one embodiment, the internal radiotherapy is brachytherapy where a solid radioactive source is placed inside a body cavity or needles are placed in the tumor. In another embodiment, the internal radiotherapy comprises administering a liquid source of radiation, typically a radionuclide (radioisotope or unsealed source). The radiation source may be orally administered or may be injected into a vein.

Optional Second Chemotherapeutic Agents

It will be appreciated that the method described herein can further comprise administration of a (second) chemotherapeutic agent. The second chemotherapeutic agent is not a liposomal mitomycin C prodrug or mitomycin C or a non-liposomal mitomycin C prodrug. The (second) chemotherapeutic agents contemplated for use in conjunction with the liposomal mitomycin C prodrug are not limited to any particular compounds or class of compounds. Several examples are now provided for illustration.

In one embodiment, the (second) chemotherapeutic agent administered in combination with liposomal-mitomycin C prodrug is gemcitabine. Gemcitabine is the generic name assigned to 2'-deoxy-2',2'-difluoro-cytidine. It is commercially available as the monohydrochloride salt, and as the .beta.-isomer. It is also known chemically as 1-(4-amino-2-oxo-1H-pyrimidin-1-yl)-2-desoxy-2,2-difluororibose. Gemcitabine is disclosed in U.S. Pat. Nos. 4,808,614 and 5,464,826, which are incorporated herein by reference for their teaching of how to synthesize, formulate, and use gemcitabine for treating susceptible neoplasms. The commercial formulation of gemcitabine hydrochloride is indicated as first-line treatment for patients with locally advanced (non-resectable Stage II or Stage III) or metastatic (Stage IV) adenocarcinoma of the pancreas, and, in combination with cisplatin or carboplatin, in patients with Non-small cell lung cancer and bladder cancer.

In another embodiment, the chemotherapeutic agent administered in combination with liposomal-mitomycin C prodrug is a vinca alkaloid, such as vinblastine, vinorelbine, vincristine, or vindesine.

In another embodiment, the chemotherapeutic agent administered in combination with liposomal-mitomycin C prodrug is an anthracycline antibiotic, such as doxorubicin or daunorubicin. These anthracycline drugs are widely used in human cancer chemotherapy. And cause DNA damage such as fragmentation and single-strand breaks. The mechanism of action of anthracyclines involves the inhibition of RNA and DNA syntheses. In one embodiment, the doxorubicin or daunorubicin are provided in liposome-entrapped form. pegylated Liposome-entrapped doxorubicin is known by the trade names of DOXIL®, CAELYX®, and LIPO-DOX®, and liposome-entrapped daunorubicin is known by the trade name DAUNOXOME®.

In another embodiment, the chemotherapeutic agent administered in combination with liposomal-mitomycin C prodrug is a taxane. Taxanes are diterpenes produced by the plants of the genus *Taxus* (yews), and are widely used as chemotherapy agents. Taxane agents include paclitaxel (TAXOL®) and docetaxel (TAXOTERE®).

In another embodiment, the chemotherapeutic agent administered in combination with liposomal mitomycin C prodrug is a fluoropyrimidine. Fluoropyrimidines are antimetabolite drugs widely used in the treatment of cancer including colorectal and breast cancer and cancers of the aerodigestive tract. The fluoropyrimidines include the drugs 5-fluorouracil (5-FU) and prodrugs of 5-FU, such as capecitabine and tegafur. In one embodiment, the fluoropyrimidine chemotherapeutic agent administered in combination with liposomal mitomycin C prodrug is a prodrug for 5-FU, such as capecitabine. Capecitabine is a fluoropyrimidine carbamate with antineoplastic activity. It is an orally administered systemic prodrug of 5'-deoxy-5-fluorouridine (5'-DFUR) which is converted to 5-fluorouracil. The chemical name for capecitabine is 5'-deoxy-5-fluoro-N-[(pentyloxy)carbonyl]-cytidine. It is marketed in the United States as XELODA® (Roche Laboratories). It is indicated for the treatment of patients with metastatic breast cancer and colorectal tumors by oral route. Capecitabine is described in U.S. Pat. No. 5,472,949.

Methods for the safe and effective administration of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J.).

Exemplary Studies in Support of the Method of Treatment

The treatment method comprises administration of liposomal-mitomycin C prodrug is provided in combination with radiation therapy. Studies were performed where mice bearing solid tumors were treated with radiation therapy and then with liposomal-mitomycin C prodrug alone or in combination with a second therapeutic agent. These studies are described in Examples 2-4. A prodrug conjugate of mitomycin C was prepared and incorporated into a liposome delivery platform (as described in Example 1), for use in the studies. The prodrug conjugate incorporated into a liposome delivery platform is referred to as "liposomal-mitomycin C prodrug."

In the study described in Example 2, mice bearing human cervical carcinoma (CaSki) tumor were treated with radiation and then with liposomal-mitomycin C prodrug or with free mitomycin C. Tumor volume was measured for 21 days and the change in tumor volume (ratio of tumor volume at day zero to tumor volume at indicated day post injection) as a function of days post injection of the chemotherapeutic agent was measured. Results are shown in FIG. 1, where the tumor-bearing mice left untreated (control, solid diamonds) were observed to experience continued tumor growth over the study period. Mice treated with radiation therapy (solid squares) had a slower rate of tumor growth than mice left untreated. Mice treated with radiation therapy and with liposomal-mitomycin C prodrug (open triangles) or treated with radiation therapy and free mitomycin C (x symbols) were observed to have little or no tumor growth.

Figure 2:
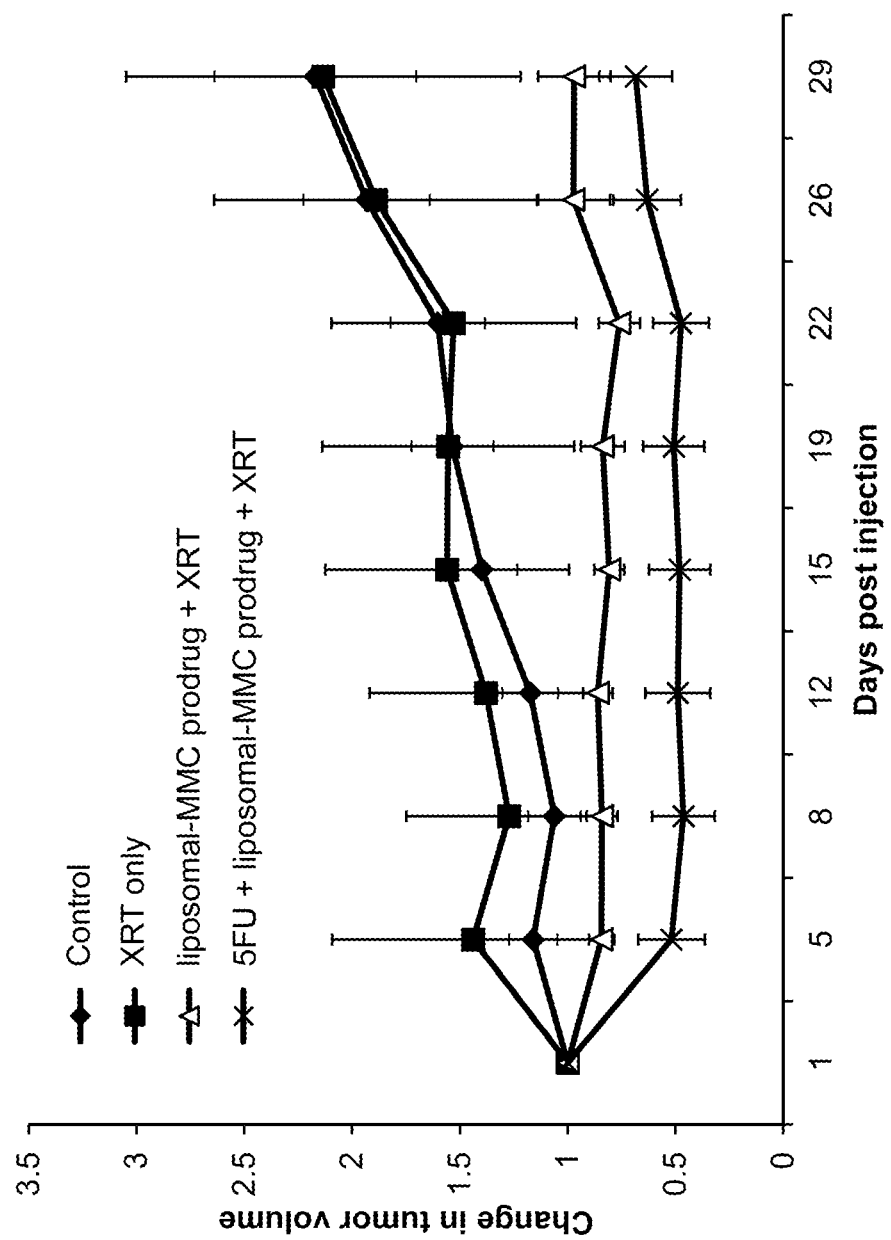
FIG. 2 shows the change in tumor volume (ratio of tumor volume at day zero to tumor volume at indicated day post injection) as a function of days post injection of chemotherapeutic agent in mice bearing a squamous cell carcinoma tumor (CaSki), where mice were left untreated (control, solid diamonds), treated with radiotherapy (irradiation) (solid squares), treated with irradiation and liposomal-mitomycin C prodrug (open triangles) or treated with radiotherapy (irradiation) and a combination therapy of liposomal-mitomycin C prodrug and 5-fluorouracil (x symbols)

In another study, described in Example 3, mice bearing human cervical carcinoma (CaSki) tumor were treated with radiotherapy alone (X-ray therapy, XRT) or in combination with liposomal-mitomycin C prodrug or with liposomal-mitomycin C prodrug and a second chemotherapeutic agent. Tumor volume was measured for 29 days and the change in tumor volume (ratio of tumor volume at day zero to tumor volume at indicated day post injection) as a function of days post injection of the chemotherapeutic agent was measured. Results are shown in FIG. 2, where the tumor-bearing mice left untreated (control, solid diamonds) were observed to experience continued tumor growth over the study period. Mice treated solely with x-ray therapy (XRT, solid squares) also experienced continued tumor growth over the study period. Mice treated with radiation therapy and with liposomal-mitomycin C prodrug (open triangles) or treated with radiation therapy and with liposomal-mitomycin C prodrug and 5-fluorouracil (x symbols) were observed to have little or no tumor growth.

Figure 3A:
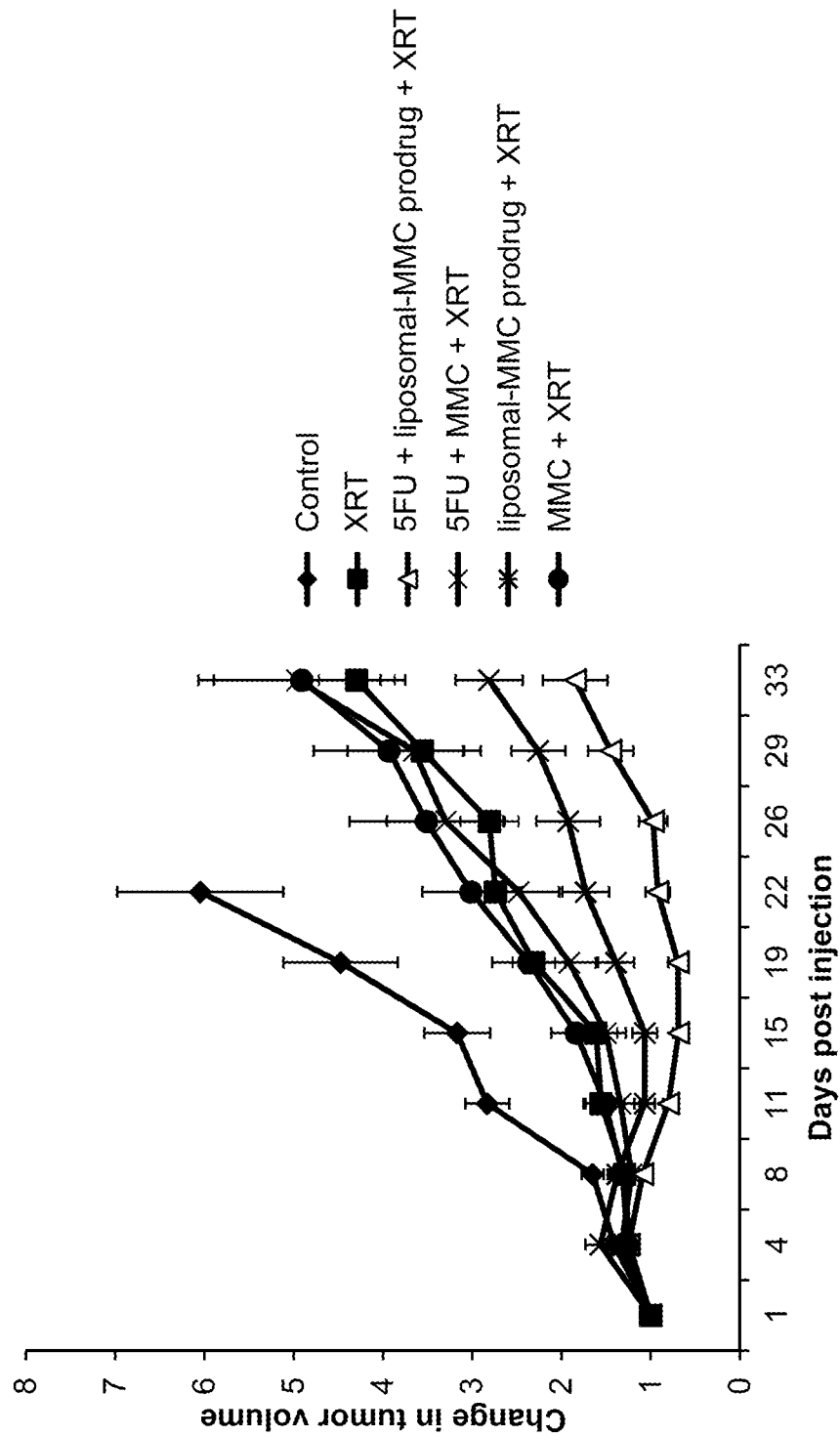
FIG. 3A shows the change in tumor volume (ratio of tumor volume at indicated day post injection to tumor volume at day of injection (day 1)) as a function of days post injection of chemotherapeutic agent in mice bearing a human colon cancer tumor (HT29), where mice were left untreated (control, solid diamonds), treated with radiotherapy (irradiation) (solid squares), treated with radiotherapy (irradiation) and liposomal-mitomycin C prodrug (* symbols), treated with irradiation and free mitomycin C (closed circles), treated with radiotherapy (irradiation) and a combination therapy of liposomal-mitomycin C prodrug and 5-fluorouracin (open triangles), or treated with radiotherapy (irradiation) and a combination therapy of free mitomycin C and 5-fluorouracil (x symbols)

Another study was performed using human colon cancer tumor xenografts in mice. As described in Example 4, solid tumors were established in mice by inoculating either with HT29 colon cancer cells or with SW480 colon cancer cells. Mice bearing HT29 solid tumors and mice bearing SW480 solid tumors were randomized into groups for treatment in separate studies. The change in tumor volume as a function of days post injection of the treatment agent is shown in FIG. 3A for HT29 tumor-bearing mice and in FIG. 3B for SW480 tumor-bearing mice. Treatments comprised of radiation therapy and liposomal-mitomycin C prodrug (* symbols) or of radiation therapy and liposomal-mitomycin C prodrug and a second agent (5-fluorouracil) (open triangles) were more effective than radiation therapy alone (solid diamond) or than radiation therapy in combination with free mitomycin C (x symbols and closed circles).

Figure 4A:
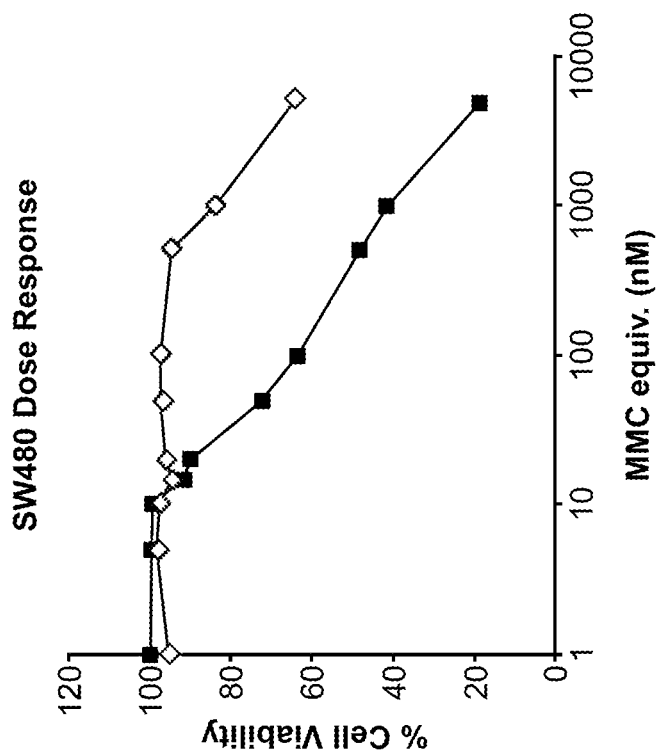
FIGS. 4A-4B are graphs of percent cell viability as a function of dose of mitomycin C in terms of nM mitomycin C equivalent, for HT29 cells (FIG. 4A) and for SW480 cells (FIG. 4B) exposed for 48 hours to liposomal-mitomycin C prodrug (triangles) or free mitomycin C (squares)
Figure 4B:
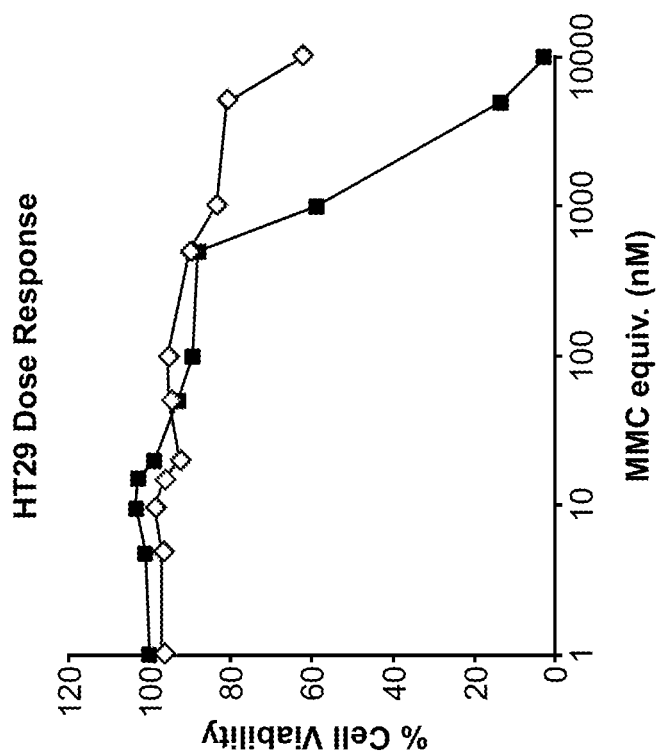

The synergistic effect of radiation therapy and liposomal-mitomycin C prodrug is further evidenced by the results from an in vitro study using the colorectal cancer cell lines HT29 and SW480 as exemplary of cancer cells. The cancer cells were treated with liposomal-mitomycin C prodrug or with free mitomycin C at doses of 1-10,000 nM mitomycin C equivalent and percent cell viability was determined after 48 hours of exposure to the drug (see Example 5 for details). The results are shown in FIGS. 4A-4B, for the HT29 cells and the SW480 cells, respectively. Free mitomycin C (squares) was more effective in killing the cells at lower doses than the liposomal-mitomycin C prodrug, where HT29 cells treated with free mitomycin C had 60% viability (FIG. 4A) at a dose of 1,000 nM mitomycin C and SW480 cells treated with free mitomycin C had 60% viability at a dose of about 100 nM mitomycin C (FIG. 4B). However, as seen in FIGS. 4C-4D, liposomal-mitomycin C prodrug in combination with radiotherapy is more effective in killing the cancer cells than is free mitomycin C in combination with radiotherapy. FIG. 4C shows the percent survival of HT29 cells treated with liposomal-mitomycin C prodrug (open diamonds) as a function of radiation dose or treated with mitomycin C (squares) as a function of radiation dose. The liposomal-mitomycin C prodrug in the presence of radiotherapy was as effective as mitomycin C at low doses of radiotherapy and more effective at radiation doses of 3-8 Gy. Because the liposomal-mitomycin C prodrug is considerably less toxic than free mitomycin C, the method of treatment comprised of administering liposomal-mitomycin C prodrug in conjunction with radiotherapy provides a treatment that is as or more effective than treatment with the mitomycin C with reduced toxicity.

The synergistic effect of radiation therapy and liposomal-mitomycin C prodrug is further evidenced by the results of another in vitro study, described in Example 6. In this study, cells in culture in vitro were exposed to irradiation. As a control, a culture with the same type of cells was not irradiated. 48 hours after irradiation, the media were collected and placed in a vial containing liposomal-mitomycin C prodrug. Aliquots from the vial were taken and analyzed for concentration of mitomycin C as a function of time. FIG. 5 shows the percent of mitomycin C released from the irradiated cells (circles) and from the control cells (no radiotherapy treatment, squares). Release of mitomycin C from the cleavage of liposomal-mitomycin C prodrug was higher at all time points for the cells exposed to radiotherapy. For example, 18 hours after the irradiated cells are mixed with liposomal-mitomycin C prodrug, about 38% of the mitomycin C was released, in contrast to about 30% of mitomycin C released in the cells not exposed to radiotherapy. At the 48 hour time point, the sample with cell medium/cells exposed to radiotherapy released about 65% of the mitomycin C, whereas the cell medium/cells not exposed to radiotherapy release about 40% of the mitomycin C. This is equivalent to a relative increase in release of ~60%. Accordingly, the results of this study demonstrate that treatment of cells or tissue with radiotherapy and with liposomal-mitomycin C prodrug provides about 20% or greater, about 25% or greater, about 30% or greater release, or at least about 20%, 25% or 30% higher release, of mitomycin C from the liposomal-mitomycin C prodrug relative to cells or tissue not treated with radiotherapy and treated with the same dose of liposomal-mitomycin C prodrug.

Mitomycin C (MMC) is a potent radiosensitizer and a well-established agent in chemoradiotherapy (CRT) for anal cancer and localized bladder cancer. However, its use is often limited by toxicity. The mitomycin C liposomal prodrug, activated by thiolytic cleavage, offers an improved toxicity profile relative to free mitomycin C. The liposomal-mitomycin C prodrug was less cytotoxic than free mitomycin C in vitro (FIGS. 4A-4B). However, following radiation liposomal-mitomycin C prodrug is as effective as free mitomycin C as a radiosensitizer for cancer cells, suggesting enhanced activation of liposomal-mitomycin C prodrug by irradiated cells (FIGS. 4C-4D). In vivo studies (Examples 2-4) demonstrated that liposomal-mitomycin C prodrug-based—radiotherapy regimens delayed tumor growth significantly more than corresponding treatment with free mitomycin C, with or without 5FU. In mice bearing HT-29 tumor xenografts, the addition of a second chemotherapeutic agent (5FU) to liposomal-mitomycin C prodrug further enhanced the tumor growth inhibitory effect of chemo-radiotherapy combination. Liposomal-mitomycin C prodrug did not cause any toxic deaths, and body weight loss in the treated mice was limited and reversible. In addition, there was less hair toxicity in mice treated with liposomal-mitomycin C prodrug despite using 2.5 fold higher MMC equivalents. Accordingly, the studies demonstrate that liposomal-mitomycin C prodrug enhances radiosensitivity of cancer cells over free mitomycin C, with or without a second chemotherapeutic agent, in vitro and in vivo, without incurring in toxicity.

Treatment Modalities and Patient Populations

As can be appreciated based on the studies described above, the method of treatment based on a liposomal-prodrug of mitomycin C and radiotherapy provides for the synergistic treatment of a neoplasia in a subject in need of treatment. Neoplasias for which the treatment methods are particularly useful include, without limitation, carcinomas, particularly those of the bladder, breast, cervix, colon, head and neck, melanoma, lung, ovary, pancreas, esophagus, anal, and stomach. In a preferred embodiment, a method is provided for the synergistic treatment of breast, colon or colorectal, stomach, esophageal and pancreatic cancers. Advantageously, the synergistic method achieves beneficial effects including reducing the growth of tumors, reducing tumor burden, and/or producing tumor regression in a mammalian host. The method also prolongs survival of a tumor-bearing mammal.

In one embodiment, radiation therapy precedes treatment with liposomal-mitomycin C prodrug, or when a second chemotherapeutic agent is given, treatment with liposomal-mitomycin C prodrug and with the second agent. In another embodiment, radiation therapy both precedes treatment with and is concurrent with treatment with liposomal-mitomycin C prodrug. These methods, wherein a prodrug of mitomycin C is administered to a subject in combination with radiotherapy, produce a synergistic antineoplastic effect. A "synergistic antineoplastic effect" refers to a greater-than-additive antineoplastic effect which exceeds that which would otherwise result from individual treatment with the prodrug alone or with radiation therapy alone. The data presented herein illustrates that a liposomal-mitomycin C prodrug administered in combination with radiation therapy unexpectedly results in a synergistic antineoplastic effect by providing greater efficacy than would result from the prodrug alone or from free mitomycin C alone or from radiation therapy alone.

One skilled in the art appreciates that a pharmaceutical composition comprising a combination of a prodrug of mitomycin C can be administered to a subject by various routes including, for example, injection directly into a tumor, orally or parenterally, such as intravenously, intramuscularly, subcutaneously, intraorbitally, intranasally, intracapsularly, intraperitoneally, intracisternally, intra-tracheally, or intra-articularly. In a particular embodiment, the composition is administered parenterally as a solution in normal saline.

The actual dosage of liposomal mitomycin C prodrug and of radiation employed may be varied depending upon the requirements of the patient and the severity of the condition being treated. Determination of the proper dosage for a particular situation is within the skill of the art. In one embodiment, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day (or for radiation therapy, week or month) if desired. Intermittent therapy (e.g., one week out of three weeks or three out of four weeks) may also be used.

Also, in accordance with the knowledge of the skilled clinician, the therapeutic protocols (e.g., dosage amounts and times of administration) can be varied in view of the observed effects of the administered therapeutic agents (i.e., antineoplastic agent(s) or radiation) on the patient, and in view of the observed responses of the disease to the administered therapeutic agents.

When a liposomal-mitomycin C prodrug is administered in combination with at least one other agent, the at least one other agent can be co-administered in the same formulation.

Alternatively, the various agents can be administered simultaneously (concurrently) in separate formulations. In addition, the agents can be administered in separate formulations, where the separate formulations are not administered simultaneously but are administered sequentially immediately with little or no time lapse between administration, or are administered sequentially during the same period of treatment, for example, during a daily or weekly period of treatment.

In another aspect, a kit or product for achieving the methods described herein is provided. The kit or product comprises a vial containing a prodrug of mitomycin C in an amount that yields a therapeutically-effective amount of mitomycin C; and instructions to administer the contents within the vial in combination with radiotherapy.

EXAMPLES

The following examples are illustrative in nature and are in no way intended to be limiting.

Example 1

Liposomal Mitomycin C Prodrug Preparation

A prodrug conjugate of mitomycin C releasably attached to a lipophilic moiety, para-diacyldiglyceroldithiobenzyl-mitomycin C, was synthesized as described in U.S. Pat. No. 7,303,760, in Example 2, incorporated by reference herein.

The para-diacyldiglyceroldithiobenzyl-mitomycin C prodrug conjugate was incorporated into a liposomal delivery vehicle as described in Example 3A of U.S. Pat. No. 7,303,760, incorporated by reference herein.

Example 2

Anti-Tumor Effect of Prodrug and Radiation Therapy

Cells from a human cervical carcinoma cell line, CaSki, were injected subcutaneously (1 million cells in 200 μL 1:1 RPMI and matrigel) into the left flank of 8 week old female Nu mice. Two weeks after inoculation, mice were treated three times with 5 Gy irradiation. Some mice were additionally treated via intravenous injection with liposomal-mitomycin C prodrug (prepared according to Example 1) or with free mitomycin C. The treatment groups are summarized below.
  Group 1: control, untreated;
  Group 2: 5 Gy irradiation given in three fractions;
  Group 3: 5 Gy irradiation given in three fractions and 30 mg/kg liposomal-mitomycin C prodrug (PROMITIL®) via tail vein intravenous injection; and
  Group 4: 5 Gy irradiation given in three fractions and 3.3 mg/kg free mitomycin C via tail vein intravenous injection.
Tumor volume was measured for 21 days in all test mice. The results are shown in FIG. 1 as change in tumor volume, i.e., ratio of tumor volume at indicated day post injection of the chemotherapeutic agent to tumor volume on day of injection.

Example 3

Anti-Tumor Effect of Prodrug and Radiation Therapy

Cells from a human cervical carcinoma cell line, CaSki, were injected subcutaneously (1 million cells in 200 μL 1:1 RPMI and matrigel) into the left flank of 8 week old female Nu mice. Two weeks after inoculation, mice were treated three times with 5 Gy irradiation and two groups of test mice were additionally treated via intravenous injection with liposomal-mitomycin C prodrug (prepared according to Example 1) or with a combination of liposomal-mitomycin C prodrug (prepared according to Example 1) and 5-fluorouracil. The treatment groups are summarized below.
  Group 1: control, untreated;
  Group 2: 5 Gy irradiation given in three fractions;
  Group 3: 5 Gy irradiation given in three fractions and 30 mg/kg liposomal-mitomycin C prodrug (PROMITIL®) via tail vein intravenous injection;
  Group 4: 5 Gy irradiation given in three fractions and 30 mg/kg liposomal-mitomycin C prodrug (PROMITIL®) and 20 mg/kg 5-fluorouracil C, via tail vein intravenous injection;
  Group 5: 5 Gy irradiation given in three fractions and 8.4 mg/kg free mitomycin C via tail vein intravenous injection; and
  Group 6: 5 Gy irradiation given in three fractions and 8.4 mg/kg free mitomycin C and 20 mg/kg 5-fluorouracil C, via tail vein intravenous injection.
Mice in Group 5 and Group 6 died two weeks after intravenous injection of the free mitomycin C due to toxicity. For the remaining test groups, the tumor volume was measured for 21 days. The results are shown in FIG. 2 as change in tumor volume, or ratio of tumor volume at indicated day post injection to tumor volume on day of injection.

Example 4

Anti-Tumor Effect of Prodrug and Radiation Therapy

Solid tumors were established in mice by inoculating either with HT29 colon cancer cells or with SW480 colon cancer cells. The mice bearing HT29 solid tumor and mice bearing SW480 solid tumor were randomized into group for treatment in separate studies as follows:
  Group 1: control, untreated;
  Group 2: 5 Gy irradiation given in three fractions;
  Group 3: 5 Gy irradiation given in three fractions and 30 mg/kg liposomal-mitomycin C prodrug (PROMITIL®) via tail vein intravenous injection;
  Group 4: 5 Gy irradiation given in three fractions and 30 mg/kg liposomal-mitomycin C prodrug (PROMITIL®) and 20 mg/kg 5-fluorouracil C, via tail vein intravenous injection;
  Group 5: 5 Gy irradiation given in three fractions and 8.4 mg/kg free mitomycin C via tail vein intravenous injection; and
  Group 6: 5 Gy irradiation given in three fractions and 8.4 mg/kg free mitomycin C and 20 mg/kg 5-fluorouracil C, via tail vein intravenous injection.
Tumor volume was measured for 33 days. The results for mice bearing an HT29 tumor are shown in FIG. 3A and for mice bearing an SW480 tumor are shown in FIG. 3B, where change in tumor volume, measured as ratio of tumor volume at indicated day post injection to tumor volume on day of injection, is presented as a function of day post injection. In both figures, the following symbols are used for each test group: Group 1, control, solid diamonds; Group 2, radiation therapy, solid squares; Group 3, radiation and liposomal-mitomycin C prodrug, * symbols; Group 4, radiation and a combination therapy of liposomal-mitomycin C prodrug and 5-fluorouracin, open triangles; Group 5, radiation and free mitomycin C, closed circles; Group 6, radiation and a combination therapy of free mitomycin C and 5-fluorouracil, x symbols.

Example 5

Anti-Tumor Effect of Prodrug and Radiation Therapy In Vitro

HT29 colon cancer cells and SW480 colon cancer cells were cultured. Cultures of each cell type were incubated for 48 hours with free mitomycin C or with liposomal-mitomycin C prodrug (prepared as described in Example 1) at doses of mitomycin C between 1-10,000 nM. The cells were washed and incubated for an additional 48 hours. Cell survival was determined using a clonogenic assay. Results are shown in FIGS. 4A-4B.

In another study, cultures of the same cell types were incubated with 10 nM mitomycin C, in the form of free mitomycin C or liposomal-mitomycin C, for 48 hours. After 48 hours, the cells were washed to remove drug and immediately irradiated with a selected dose of radiation of between 1-8 Gy. Cell survival was determined using a clonogenic assay. Results are shown in FIGS. 4C-4D.

Example 6

In Vitro Release of Mitomycin C Form Liposomes Comprising Mitomycin C Prodrug in Presence of Radiotherapy Colorectal cancer cell line HT29 cells were cultured in vitro in a petri dish in a cell medium. Upon confluence, the cells were exposed to 20 Gy radiation. As a control, a separate culture of cells was not irradiated. The cells were incubated for 48 hours. The culture medium from the control cells and the irradiated cells were collected and placed in separate vials containing liposomal-mitomycin C prodrug (prepared as described in Example 1) at a concentration of 2.5 mg/ml. Cleavage of prodrug and release of mitomycin C from the liposomal composition was determined as a function of time by taking aliquots of the fluid in each vial and measuring for mitomycin C concentration. The results are shown in FIG. 5, where the percent of mitomycin C released from the irradiated cells (circles) and from the control cells (no radiotherapy treatment; squares) is shown over the 80 hour test period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A treatment method, comprising:
   providing to a subject in need a prodrug of mitomycin C in an amount that yields a therapeutically-effective amount of mitomycin C, wherein the prodrug is a conjugate of mitomycin C releasably attached to a lipophilic moiety, and is of the formula:

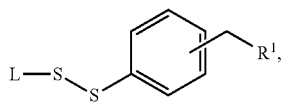

wherein L is a hydrophobic moiety, $R^1$ represents a mitomycin C residue, the $-CH_2R^1$ group is selected from the ortho position and the para position; and
   instructing to administer, or administering, in combination with the prodrug radiation therapy.

2. The method of claim 1, wherein the providing a prodrug of mitomycin C comprises providing via injection a prodrug of mitomycin C.

3. The method of 1, wherein providing a prodrug of mitomycin C comprises providing a composition comprising a liposomal formulation, where the prodrug of mitomycin C is incorporated into liposomes in the liposomal formulation.

4. The method of claim 3, wherein the providing via injection comprises intravenous, intraarterial, intraperitoneal, intrapleural, intrathecal, intravesical or intratumoral injection.

5. The method of claim 1, wherein instructing comprises instructing to administer the radiation therapy concurrently or sequentially with the prodrug.

6. The method of claim 1, wherein the radiation therapy is an external radiation therapy.

7. A treatment regimen for a subject with cancer, comprising:
   administering a prodrug of mitomycin C in an amount that yields a therapeutically-effective amount of mitomycin C, wherein the prodrug is a conjugate of mitomycin C releasably attached to a lipophilic moiety, and is of the formula:

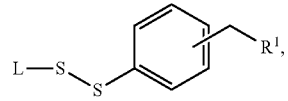

wherein L is a hydrophobic moiety, $R^1$ represents a mitomycin C residue, the $-CH_2R^1$ group is selected from the ortho position and the para position; and
   administering radiation therapy;
   whereby by said administering steps provide a reduction in tumor volume or prolong survival of the subject, when compared to that achieved by administering the prodrug alone or radiation therapy alone.

8. The regimen of claim 7, wherein the lipophilic moiety is incorporated into a liposome.

9. The regimen of claim 7, wherein the administering a prodrug of mitomycin C comprises administering via injection.

10. The regimen of claim 9, wherein the administering via injection comprises intravenous, intraarterial, intraperitoneal, intrapleural, intrathecal, intravesical or intratumoral injection.

11. The regimen of claim 7, wherein administering radiation therapy comprises administering the radiation therapy prior to, concurrently with or sequentially with administering the prodrug.

12. The regimen of claim 7, wherein the radiation therapy is an external radiation therapy.

13. The regimen of claim 7, wherein the cancer is brain cancer, head and neck cancer, lung cancer, breast cancer, esophageal cancer, stomach cancer, pancreatic cancer, colorectal cancer, or bladder cancer.

14. A method for treating a solid tumor, comprising:
   providing a prodrug of mitomycin C in an amount that yields a therapeutically-effective amount of mitomycin C, wherein the prodrug is a conjugate of mitomycin C releasably attached to a lipophilic moiety, and is of the formula:

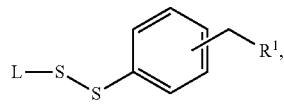

wherein L is a hydrophobic moiety, $R^1$ represents a mitomycin C residue, the —$CH_2R^1$ group is selected from the ortho position and the para position; and providing instructions to administer in combination with the prodrug a radiation therapy.

15. The method of claim 14, wherein the lipophilic moiety is incorporated into a liposome.

16. The method of claim 14, wherein the providing a prodrug of mitomycin C comprises providing the prodrug in a form suitable for administration via injection.

17. The method of claim 14, wherein providing a prodrug of mitomycin C comprises providing a composition comprising a liposomal formulation, where a prodrug of mitomycin C is incorporated into liposomes in the liposomal formulation.

18. The method of claim 14, wherein providing instructions comprises providing instructions to administer the radiation therapy prior to, concurrently with or sequentially with administering the prodrug.

19. The method of claim 14, wherein the radiation therapy is an external radiation therapy.

20. A product, comprising:

a vial containing a prodrug of mitomycin C in an amount that yields a therapeutically-effective amount of mitomycin C, wherein the prodrug is a conjugate of mitomycin C releasably attached to a lipophilic moiety, and is of the formula:

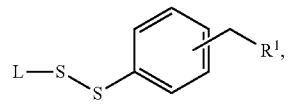

wherein L is a hydrophobic moiety, $R^1$ represents a mitomycin C residue, the —$CH_2R^1$ group is selected from the ortho position and the para position; and instructions to administer the contents within the vial in combination with radiation therapy.

* * * * *